United States Patent [19]
Cherng-Chyi et al.

[11] Patent Number: 5,110,493
[45] Date of Patent: May 5, 1992

[54] OPHTHALMIC NSAID FORMULATIONS CONTAINING A QUATERNARY AMMONIUM PRESERVATIVE AND A NONIONIC SURFACTANT

[75] Inventors: Roger F. Cherng-Chyi; Deborah M. Lidgate, both of Los Altos, Calif.

[73] Assignee: Syntex (U.S.A.) Inc., Palo Alto, Calif.

[21] Appl. No.: 624,027

[22] Filed: Dec. 7, 1990

Related U.S. Application Data

[63] Continuation of Ser. No. 96,173, Sep. 11, 1987, abandoned.

[51] Int. Cl.$^5$ ............................................. A61K 31/40
[52] U.S. Cl. ................................... 514/413; 252/106; 514/912; 514/914
[58] Field of Search ........................ 514/413, 912, 914; 252/106

[56] References Cited

U.S. PATENT DOCUMENTS

| | | | |
|---|---|---|---|
| 4,087,538 | 2/1978 | Portnoff | 514/914 |
| 4,087,539 | 2/1978 | Muchowski et al. | 424/274 |
| 4,089,969 | 3/1978 | Muchowski et al. | 424/274 |
| 4,097,579 | 5/1978 | Muchowski et al. | 424/274 |
| 4,230,724 | 10/1980 | Cooper et al. | 514/912 |
| 4,232,038 | 10/1980 | Kluge et al. | 424/274 |
| 4,336,151 | 3/1982 | Like et al. | 252/106 |
| 4,336,152 | 3/1982 | Like et al. | 252/106 |
| 4,454,151 | 2/1984 | Waterbury | 424/274 |
| 4,474,751 | 10/1984 | Haslam et al. | 514/912 |
| 4,474,811 | 10/1984 | Masuda et al. | 514/912 |
| 4,500,538 | 2/1985 | Woltersdorf | 514/367 |
| 4,559,343 | 12/1985 | Han et al. | 514/264 |
| 4,607,038 | 8/1986 | Ogata et al. | 514/291 |

FOREIGN PATENT DOCUMENTS

| | | |
|---|---|---|
| 0038698 | 10/1981 | European Pat. Off. |
| 3026402 | 2/1982 | Fed. Rep. of Germany |
| 23318 | 2/1985 | Japan |
| 8504106 | 9/1985 | PCT Int'l Appl. |
| 830864 | 3/1960 | United Kingdom |

OTHER PUBLICATIONS

Fraser-Smith et al., "Effect of Ketorolac on Pseudomonas aeruginosa . . ."; J. Ocular Pharmacol., v 4(2), pp. 101-109 (1988).

"Influence of (Ethoxy)$_5$ Octyl Phenol on the Antibacterial Properties of Preservatives", M. T. Nadir, et al., Journal of Pharmacy and Pharmacology, vol. 29, Supplement, Dec. 1977, p. 67P.

"Ocufen (flurbiprofen sodium) 0.03% Liquifilm sterile ophthalmic solution," Allergan, product description sheet, one page.

CTFA Cosmetic Ingredient Dictionary; Cosmetic, Toiletry and Fragrance Association, Inc., pp. 187-188.

Schmolka, Irving R., "The Synergistic Effects of Nonionic Surfactants Upon Cationic Germicidal Agents", J. Soc. Cosmet. Chem. 24, 577-592 (Aug. 9, 1973).

The Condensed Chemical Dictionary, Seventh Ed., Reinhold Publishing Co., N.Y. p. 985.

McCutcheon's, "Emulsifiers & Detergents," North American Edition, 1982, p. 154.

*Primary Examiner*—A. Lionel Clingman
*Assistant Examiner*—Mary C. DiNunzio
*Attorney, Agent, or Firm*—Derek P. Freyberg; Karl Bozicevic

[57] ABSTRACT

Stable, clear, antimicrobially effective, ophthalmic formulations include an ophthalmologically effective amount of a drug, especially a —COOH group-containing drug or a NSAID, and a preservative system formed of a quaternary ammonium preservative and a nonionic surfactant, all in an aqueous vehicle. These formulations are useful for treating diseases that are either caused by, associated with or accompanied by inflammatory processes, including, among others, glaucoma, cystoid macular edema, uveitis, diabetic retinopathy and conjunctivitis, or any trauma caused by eye surgery or eye injury.

16 Claims, No Drawings

OPHTHALMIC NSAID FORMULATIONS CONTAINING A QUATERNARY AMMONIUM PRESERVATIVE AND A NONIONIC SURFACTANT

CROSS-REFERENCE TO RELATED APPLICATION

This application is a continuation of our copending application Ser. No. 07/096,173, filed Sep. 11, 1987 now abandoned.

BACKGROUND OF THE INVENTION

The present invention relates to improved ophthalmic formulations, particularly to ophthalmic formulations for anti-inflammatory drugs, and specifically to an improved preservative system for ophthalmic formulations of carboxyl ("—COOH") group-containing drugs, especially non-steroidal anti-inflammatory drugs ("NSAIDs").

The invention also relates to methods of using these formulations for treating diseases that are either caused by, associated with or accompanied by inflammatory processes, including, among others, glaucoma, cystoid macular edema, uveitis, diabetic retinopathy and conjunctivitis, or any trauma caused by eye surgery or eye injury.

The topical use of NSAIDs, particularly pyrrolo pyrroles, in the treatment of ophthalmic diseases was first taught in U.S. Pat. No. 4,454,151, where NSAID compounds (such as those described in U.S. Pat. Nos. 4,089,969; 4,232,038; 4,087,539 and 4,097,579) were exemplified in formulation with $NaH_2PO_4.H_2O$, $Na_2HPO_4.H_2O$, NaCl, benzalkonium chloride ("BAC") and sterilized water. While the formulations described in the '151 patent were efficacious, a complex was found to form between the NSAID and the BAC. The formulations did not, therefore, have the stability desired for shelf life in commercial applications. A reasonable minimum shelf life is at least about one year, representing sufficient time to package, ship, and store a formulation without having to replace expired stock too frequently. Thus, the present invention entails an improvement over the formulations described in the '151 patent.

In general, an ophthalmic formulation contains an active compound and various ophthalmologically acceptable excipients, in the form of a solution, an ointment, a suspension, etc. An excipient is ophthalmologically acceptable if it is non-irritating to the eye and if its active ingredient penetrates the blood-aqueous barrier and/or difuses through the various ocular substructures to the site where it is pharmacologically active. The excipients can include a tonicifier, a preservative, a surfactant, a buffering system, a chelating agent, a viscosity agent as well as other stabilizing agents. Ophthalmic formulations must be sterile, and if intended for multiple dosing regimens, must be preserved with an effective anti-microbial agent.

Organo-mercurials (e.g., thimerosal, phenylmercuric acetate and phenylmercuric nitrate) have been used extensively as the preservative in ophthalmic solutions. These compounds, however, pose difficulties due to potential mercury toxicity as well as poor chemical stability. Benzalkonium chloride, a quaternary ammonium compound, has been widely used in ophthalmic solutions, and is considered to be the preservative of choice. However, BAC has typically been considered to be incompatible with anionic drugs (e.g., salicylates or nitrates, etc.) and can be inactivated by surfactants.

Many NSAIDs (such as ketorolac, indomethacin, flurbiprofen and suprofen) are being developed for ocular use because of their activity as anti-inflammatory agents as well as their ability to prevent cystoid macular edema.

These NSAIDs have proven to be incompatible with quaternary ammonium compounds such as BAC because they can form a complex with them, rendering the preservative less available to serve its function, as is the case with other ophthalmic drugs that contain a —COOH group. Thus, less preferred preservatives have been used in such ophthalmic formulations. For example, Ocufen Ophthalmic solution, the first NSAID (flurbiprofen) approved by the FDA for ophthalmic use, incorporates thimerosal (with EDTA) as its preservative system.

It has remained desired to provide a stable, clear, antimicrobially effective ophthalmic formulation for NSAIDs using BAC as the preservative, and an improved preservative system for —COOH group containing ophthalmic drugs.

SUMMARY OF THE INVENTION

It has now been discovered that stable, i.e., clear and antimicrobially effective, NSAID-containing ophthalmic formulations can be prepared that do not include an organo-mercurial preservative.

In one aspect of the invention, these compositions include an ophthalmologically effective amount of a NSAID, a quaternary ammonium preservative and a stabilizing amount of a nonionic surfactant, all in an aqueous vehicle.

Another aspect is an antimicrobially effective preservative system for ophthalmic drugs having a —COOH group, including a quaternary ammonium preservative and a stabilizing amount of a nonionic surfactant.

In a third aspect of the invention, methods for treating ophthalmic diseases in mammals using the ophthalmic pharmaceutical formulations of the invention are also disclosed. These diseases are those that are either caused by, associated with or accompanied by inflammatory processes, including, among others, glaucoma, cystoid macular edema, uveitis, diabetic retinopathy and conjunctivitis, or any trauma caused by eye surgery or eye injury.

DETAILED DESCRIPTION OF THE PREFERRED EMBODIMENTS

DEFINITIONS

As used herein, the term "NSAID" means an ophthalmologically acceptable non-steroidal anti-inflammatory drug.

As used herein, the term "q.s." means adding a quantity sufficient to achieve a stated function, e.g., to bring a solution to the desired volume (i.e., 100%).

As used herein, the term "treatment" or "treating" means any treatment of a disease in a mammal, including:

(i) preventing the disease, that is, causing the clinical symptoms of the disease not to develop;

(ii) inhibiting the disease, that is, arresting the development of clinical symptoms; and/or (iii) relieving the disease, that is, causing the regression of clinical symptoms.

As used herein, the term "effective amount" means a dosage sufficient to provide treatment for the disease state being treated. This will vary depending on the patient, the disease and the treatment being effected.

As used herein, the term "antimicrobially effective" means ability to withstand the U.S. Pharmacopia antimicrobial challenge.

As used herein, the term "stabilizing" means keeping a formulation clear and antimicrobially effective for its minimum reasonable shelf life, e.g., at least one year.

FORMULATIONS

The formulations of the present invention include a NSAID active agent in an effective amount for ophthalmic treatment, a quaternary ammonium preservative, a stabilizing amount of a nonionic surfactant, optionally including other excipients such as a chelating agent, a tonicifier, a buffering system, a viscosity agent as well as other stabilizing agents. Ophthalmic solutions and suspensions typically contain an aqueous vehicle rather than an oily vehicle. Ophthalmic formulations must be sterile, and if intended for multiple dosing regimens, must be antimicrobially effective for their minimum reasonable shelf life, e.g., at least one year, and preferably two to three years or more. The ingredients used in the formulations of the present invention are typically commercially available or can be made by methods readily known to those skilled in the art.

Pharmaceutical ophthalmic formulations typically contain an effective amount, e.g., 0.001% to 10% wt/vol., most preferably 0.005% to 1% of an active ingredient (e.g., the NSAID of the present invention). The amount of active ingredient will vary with the particular formulation and the disease state for which it is intended. The total concentration of solutes should be such that, if possible, the resulting solution is isotonic with the lacrimal fluid (though this is not absolutely necessary) and has a pH in the range of 6-8.

The formulations of the present invention are prepared as solutions incorporating the above-described ingredients within the following approximate ranges:

| Ingredient | Amount |
|---|---|
| Active Agent | 0.001% to 10.0% wt/vol.; |
| Preservative | 0.001% to 1.0% wt/vol.; |
| Surfactant | 0.001% to 1.0% wt/vol.; |
| Other Excipients | 0% to 10.0% wt/vol.; and |
| Purified Water | q.s. to 100%. |

Optional other excipients, such as a chelating agent and a tonicifier, are used in the following approximate proportions:

| Ingredient | Amount |
|---|---|
| Chelating agent | 0.01% to 1.0% wt/vol.; |
| Tonicifier | q.s. to achieve isotonicity with lacrimal fluid; and |
| 1N NaOH or 1N HCl | q.s to adjust pH to 6.0 to 8.0. |

In a preferred ophthalmic NSAID solution, the ingredients are combined in the following proportions:

| Ingredient | Amount |
|---|---|
| NSAID | 0.50% wt/vol.; |
| BAC (50% aq. soln.) | 0.02% wt/vol.; |
| Octoxynol 40 (70% aq. soln.) | 0.01% wt/vol.; |
| EDTA Na$_2$ | 0.10% wt/vol.; |
| NaCl | q.s. for isotonicity with lacrimal fluid; |
| 1N NaOH or 1N HCl | q.s. to adjust pH to 7.4 ± 0.4; and |
| Purified Water | q.s. to 100%. |

The invention relates primarily to formulations having as the active agent ophthalmologically acceptable drugs (including the esters and pharmaceutically acceptable salts thereof) that can form a complex with a quaternary ammonium compound, particularly NSAIDs and drugs with a carboxyl group.

NSAIDs useful in the practice of this invention include, for example, ketorolac (and the other compounds described as being ophthalmologically effective in U.S. Pat. No. 4,454,151 to Waterbury, issued Jun. 12, 1984, the pertinent portions of which are incorporated herein by reference), indomethacin, flurbiprofen sodium, and suprofen, including the esters and pharmaceutically acceptable salts thereof.

Preservatives useful in the formulations of the present invention include quaternary ammonium compounds, such as cetyltrimethylammonium bromide, cetylpyridinium chloride and preferably, benzalkonium chloride.

The nonionic surfactants useful in the formulations of the present invention are preferably polyoxyethylated surfactants including polyoxyethylene hydrogenated vegetable oils, such as polyethylene 60 hydrogenated castor oil, manufactured and sold by Kao Corp. of Japan under the trade name Emanon CH-60, and preferably ethoxylated octylphenol compounds, such as Octoxynol 10 and most preferably Octoxynol 40, manufactured and sold by GAF under the trade name Igepal CA897 (a 70% aqueous solution of Octoxynol 40).

Among the optional excipients, the chelating agents useful in the formulations of the present invention include 8-hydroxyquinoline sulfate, citric acid, and preferably disodium edetate. Under certain conditions, the chelating agent may also enhance the anti-microbial effect due to its ability to render essential metal ions unavailable to the microbes.

Buffering systems optionally useful in the formulations of the present invention are based on, for example, citrate, borate, or phosphate.

Tonicifiers optionally useful in the formulations of the present invention include dextrose, potassium chloride and/or sodium chloride, preferably sodium chloride.

Viscosity agents optionally useful in the formulations of the present invention include the cellulose derivatives such as hydroxypropylmethyl cellulose, sodium carboxymethylcellulose, and hydroxyethylcellulose.

Other optional excipients useful in the formulations of the present invention include stabilizing agents such as antioxidants, e.g., sodium metabisulfate and ascorbic acid, depending on the NSAID used.

These formulations are prepared by dissolving the solutes (e.g., the NSAID, the preservative, the surfactant, the chelating agent, and the buffering agent) in a suitable quantity of water, adjusting the pH to about 6-8, preferably 6.8-8.0 and most preferably 7.4, making a final volume adjustment to 100% with additional water, and sterilizing the preparation using any suitable method known to those in the art.

It has been discovered that ophthalmic formulations incorporating the preservative system of the invention are physically stable (i.e., remain clear) and functionally stable (i.e., remain antimicrobially effective) for at least the minimum reasonable shelf life of such products.

PREFERRED FORMULATIONS

The preferred preservative system of the invention includes a quaternary ammonium preservative and a stabilizing amount of a nonionic surfactant.

The preferred ophthalmic formulation of the invention includes a NSAID active agent in an effective amount for ophthalmic treatment and an antimicrobially effective amount of the above-described preferred preservative system.

The preferred preservative of the invention is benzalkonium chloride.

The preferred surfactant of the invention is Octoxynol 40, especially when combined with benzalkonium chloride.

The preferred chelating agent of the invention is disodium edetate, especially when combined with benzalkonium chloride and Octoxynol 40.

The preferred ophthalmic solutions of the invention include a NSAID, benzalkonium chloride, Octoxynol 40 and disodium edetate.

A preferred ophthalmic NSAID solution has the following formulation:

| Ingredient | Amount |
| --- | --- |
| NSAID | 0.50% wt/vol. |
| BAC (50% aq. soln.) | 0.02% wt/vol. |
| Octoxynol 40 (70% aq. soln.) | 0.01% wt/vol. |
| EDTA Na$_2$ | 0.10% wt/vol. |
| NaCl | q.s. for isotonicity with lacrimal fluid |
| 1N NaOH or 1N HCl | q.s. to adjust pH to 7.4 ± 0.4 |
| Purified Water | q.s to 100% |

Most preferred is the ophthalmic solution according to the above formulation wherein the NSAID is Ketorolac Tromethamine.

UTILITY AND ADMINISTRATION

This invention is directed to NSAID ophthalmic formulations and a method useful for treating ophthalmic diseases in mammals. These diseases are either caused by, associated with or accompanied by inflammatory processes, including, among others, glaucoma, cystoid macular edema, uveitis, diabetic retinopathy and conjunctivitis, or any trauma caused by eye surgery or eye injury.

The method of this invention is both curative and preventative. Where applied, for example, pre-surgically or immediately post-traumatically, i.e. before inflammation develops, it prevents development of inflammation. When applied directly to the eye suffering from any of the named opthalmic diseases, it supresses already developed inflammatory processes.

Opthalmic formulations are typically administered by topical application to the eyelids or for instillation into the space (cul-de-sac) between the eyeball and the eyelids, by topically applied ophthalmic solutions, suspensions or ointments, or by subconjunctival injection.

The dosage level will, of course, depend on the concentration of the drops, the condition of the subject and the individual magnitude of responses to treatment. However, typical dosage ranges might be about 2-10 drops of 0.1% solution of active ingredient per day.

For a more detailed discussion of ophthalmic formulations, their preparation and administration, see *Remington's Pharmaceutical Sciences*, 15th Ed., pages 1489-1504, (1975).

TESTING

Ophthalmic formulations such as the solutions of the present invention are typically tested for physical stability, chemical stability, and preservative efficacy, both when they are first manufactured and after a fixed period of time (e.g., after two years). They are generally considered to be safe and clinically acceptable if proven to be well tolerated in the eye.

Physical stability is determined by observation of a solution after expiration of a fixed period of time. A solution is considered to be physically stable if its appearance (e.g., color and clarity) does not change and if the pH remains constant, within acceptable limits. Chemical stability involves a routine chemical analysis of the solution, to be sure that its active ingredient and the excipients have not changed after a fixed period of time.

Preservative efficacy is tested by the procedure described in the U.S. Pharmacopia Compendiary, whereby a solution is challenged with a microbe and a determination is made as to whether the microbe survives in it.

EXAMPLES

The following examples are given to enable those skilled in the art to more clearly understand and to practice the present invention. They should not be considered as a limitation on the scope of the invention, but merely as being illustrative and representative thereof.

EXAMPLE 1

This example illustrates the preparation of a representative pharmaceutical formulation for ophthalmic administration containing the NSAID Ketorolac Tromethamine.

| Ingredient | Amount |
| --- | --- |
| Ketorolac Tromethamine | 0.50% wt/vol. |
| BAC (50% aq. soln.) | 0.02% wt/vol. |
| Octoxynol 40 (70% aq. soln.) | 0.01% wt/vol. |
| EDTA Na$_2$ | 0.10% wt/vol. |
| NaCl | 0.79% wt/vol. |

The above ingredients are mixed, adding purified water until they are dissolved, the pH is adjusted to 7.4±0.4 and the balance of the formulation is made up with purified water, adding a quantity sufficient to make 100% volume. The solution is then sterilized.

Other NSAIDs, such as those described above, can be used as the active compound in the preparation of the formulation of this example.

EXAMPLE 2

This example illustrates the preparation of a representative pharmaceutical formulation for ophthalmic administration containing the NSAID Ketorolac Tromethamine.

| Ingredient | Amount |
| --- | --- |
| Ketorolac Tromethamine | 0.50% wt/vol. |
| BAC (50% aq. soln.) | 0.01% wt/vol. |
| Octoxynol 40 (70% aq. soln.) | 0.02% wt/vol. |
| EDTA Na$_2$ | 0.20% wt/vol. |
| NaCl | 0.79% wt/vol. |

The above ingredients are mixed, adding purified water until they are dissolved, the pH is adjusted to 7.4±0.4 and the balance of the formulation is made up with purified water, adding a quantity sufficient to make 100% volume. The solution is then sterilized.

Other NSAIDs, such as those described above, can be used as the active compound in the preparation of the formulation of this example.

EXAMPLE 3

This example illustrates the preparation of a representative pharmaceutical formulation for ophthalmic administration containing the NSAID Ketorolac Tromethamine.

| Ingredient | Amount |
| --- | --- |
| Ketorolac Tromethamine | 0.10% wt/vol. |
| BAC (50% aq. soln.) | 0.004% wt/vol. |
| Octoxynol 40 (70% aq. soln.) | 0.004% wt/vol. |
| EDTA Na$_2$ | 0.05% wt/vol. |
| NaCl | 0.88% wt/vol. |

The above ingredients are mixed, adding purified water until they are dissolved, the pH is adjusted to 7.4±0.4 and the balance of the formulation is made up with purified water, adding a quantity sufficient to make 100% volume. The solution is then sterilized.

Other NSAIDs, such as those described above, can be used as the active compound in the preparation of the formulation of this example.

EXAMPLE 4

This example illustrates the preparation of a representative pharmaceutical formulation for ophthalmic administration containing the NSAID flurbiprofen sodium.

| Ingredient | Amount |
| --- | --- |
| Flurbiprofen Sodium | 0.03% wt/vol. |
| BAC (50% aq. soln.) | 0.02% wt/vol. |
| Octoxynol 40 (70% aq. soln.) | 0.01% wt/vol. |
| EDTA Na$_2$ | 0.10% wt/vol. |
| NaCl | 0.90% wt/vol. |

The above ingredients are mixed, adding purified water until they are dissolved, the pH is adjusted to 7.4±0.4 and the balance of the formulation is made up with purified water, adding a quantity sufficient to make 100% volume. The solution is then sterilized.

Other ophthalmic drugs and NSAIDs, such as those described above, can be used as the active compound in the preparation of the formulation of this example.

EXAMPLE 5

Physical stability of the formulations of the present invention is measured by preparing clear formulations, e.g., according to the foregoing Examples, sealing them in sterilized containers, and observing the clarity of the solution after a period of one month and again after five months. Solutions that remain clear are considered stable in this procedure.

The formulations of the present invention have proven to be stable when tested in accordance with the above procedure. Formulations using surfactants other than the nonionic surfactants of the invention did not remain clear and were not stable.

EXAMPLE 6

Preservative efficacy of the formulations of the present invention is measured by preparing formulations, e.g., according to the foregoing Examples, and subjecting them to the U.S. Pharmacopia antimicrobial challenge.

The formulations of the present invention demonstrate preservative efficacy when tested in accordance with the above procedure.

While the present invention has been described with reference to the specific embodiments thereof, it should be understood by those skilled in the art that various changes may be made and equivalents may be substituted without departing from the true spirit and scope of the invention. In addition, many modifications may be made to adapt a particular situation, material, composition of matter, process, process step or steps, to the objective, spirit and scope of the present invention. All such modifications are intended to be within the scope of the claims appended hereto.

What is claimed is:

1. An ophthalmologically acceptable non-steroidal anti-inflammatory drug formulation, comprising:
    an ophthalmologically acceptable non-steroidal anti-inflammatory carboxyl group-containing drug in an effective amount for ophthalmic treatment between 0.001% and 10.0% wt/vol;
    a quaternary ammonium preservative in an antimicrobially effective amount between 0.001% and 1.0% wt/vol;
    an ethoxylated alkyl phenol that conforms generally to the formula: $C_8H_{17}C_6H_4(OCH_2CH_2)_nOH$ where n has an average value of 40 in a stabilizing amount between 0.001% and 1.0% wt/vol; and an aqueous vehicle q.s. to 100%.

2. The ophthalmologically acceptable non-steroidal anti-inflammatory drug formulation of claim 1 wherein said quaternary ammonium preservative is benzalkonium chloride.

3. The ophthalmologically acceptable non-steroidal anti-inflammatory drug formulation of claim 2 wherein said ophthalmologically acceptable non-steroidal anti-inflammatory carboxyl group-containing drug is selected from the group selected from ketorolac, indomethacin, flurbiprofen, and suprofen.

4. The ophthalmologically acceptable non-steroidal anti-inflammatory drug formulation of claim 3 wherein said ophthalmologically acceptable non-steroidal anti-inflammatory carboxyl group-containing drug is ketorolac tromethamine.

5. The ophthalmologically acceptable non-steroidal anti-inflammatory drug formulation of claim 1, further comprising:
- a chelating agent in an amount between 0.01% and 1.0% wt/vol;
- a tonicifier q.s. to achieve isotonicity with lacrimal fluid; and
- 1N NaOH or 1N HCl q.s. to adjust pH to 7.4±0.4.

6. The ophthalmologically acceptable non-steroidal anti-inflammatory drug formulation of claim 1 comprising:

| | |
|---|---|
| ophthalmologically acceptable non-steroidal anti-inflammatory carboxyl group-containing drug | 0.50% wt/vol; |
| BAC (50% aq. soln.) | 0.02% wt/vol; |
| an ethoxylated alkyl phenol that conforms generally to the formula: $C_8H_{17}C_6H_4(OCH_2CH_2)_nOH$ where n has an average value of 40 (70% aq. soln.) | 0.01% wt/vol; |
| Na$_2$EDTA | 0.10% wt/vol; |
| NaCl | q.s. for isotonicity with lacrimal fluid; |
| 1N NaOH or 1N HCl | q.s. to pH 7.4 ± 0.4; and |
| purified water | q.s. to 100%. |

7. The ophthalmologically acceptable non-steroidal anti-inflammatory drug formulation of claim 6 comprising:

| | |
|---|---|
| ketorolac tromethamine | 0.50% wt/vol; |
| BAC (50% aq. soln.) | 0.02% wt/vol; |
| an ethoxylated alkyl phenol that conforms generally to the formula: $C_8H_{17}C_6H_4(OCH_2CH_2)_nOH$ where n has an average value of 40 (70% aq. soln.) | 0.01% wt/vol; |
| Na$_2$EDTA | 0.10% wt/vol; |
| NaCl | 0.79% wt/vol; |
| 1N NaOH or 1N HCl | q.s. to pH 7.4 ± 0.4; and |
| purified water | q.s. to 100%. |

8. A method of treating an ophthalmic disease caused by, associated with, or accompanied by inflammatory processes, comprising administering to a mammal suffering therefrom a formulation comprising:
- an ophthalmologically acceptable non-steroidal anti-inflammatory carboxyl group-containing drug in an effective amount for ophthalmic treatment between 0.001% and 10.0% wt/vol;
- a quaternary ammonium preservative in an antimicrobially effective amount between 0.001% and 1.0% wt/vol;
- an ethoxylated alkyl phenol that conforms generally to the formula: $C_8H_{17}C_6H_4(OCH_2CH_2)_nOH$ where n has an average value of 40 in a stabilizing amount between 0.001% and 1.0% wt/vol; and an aqueous vehicle q.s. to 100%.

9. The method of claim 8, wherein said quaternary ammonium preservative is benzalkonium chloride.

10. The method of claim 9 wherein said ophthalmologically acceptable non-steroidal anti-inflammatory carboxyl group-containing drug is selected from the group selected from ketorolac, indomethacin, flurbiprofen, and suprofen.

11. The method of claim 10 wherein said ophthalmologically acceptable non-steroidal anti-inflammatory carboxyl group-containing drug is ketorolac tromethamine.

12. The method of claim 8 wherein the formulation further comprises:
- a chelating agent in an amount between 0.01% and 1.0% wt/vol;
- a tonicifier q.s. to achieve isotonicity with lacrimal fluid; and
- 1N NaOH or 1N HCl q.s. to adjust pH to 7.4±0.4.

13. The method of claim 8 wherein the formulation comprises:

| | |
|---|---|
| ophthalmogically acceptable non-steroidal anti-inflammatory carboxyl group-containing drug | 0.50% wt/vol; |
| BAC (50% aq. soln.) | 0.02% wt/vol; |
| an ethoxylated alkyl phenyl that conforms generally to the formula: $C_8H_{17}C_6H_4(OCH_2CH_2)_nOH$ where n has an average value of 40 (70% aq. soln.) | 0.01% wt/vol; |
| Na$_2$EDTA | 0.10% wt/vol; |
| NaCl | q.s. for isotonicity with lacrimal fluid; |
| 1N NaOH or 1N HCl | q.s to pH 7.4 ± 0.4; and |
| purified water | q.s. to 100%. |

14. The method of claim 13 wherein the formulation comprises:

| | |
|---|---|
| ketorolac tromethamine | 0.50% wt/vol; |
| BAC (50% aq. soln.) | 0.02% wt/vol; |
| an ethoxylated alkyl phenol that conforms generally to the formula: $C_8H_{17}C_6H_4(OCH_2CH_2)_nOH$ where n has an average value of 40 (70% aq. soln.) | 0.01% wt/vol; |
| Na$_2$EDTA | 0.10% wt/vol; |
| NaCl | 0.79% wt/vol; |
| 1N NaOH or 1N HCl | q.s. to pH 7.4 ± 0.4; and |
| purified water | q.s. to 100%. |

15. An antimicrobially effective preservative system for an ophthalmologically acceptable non-steroidal anti-inflammatory carboxyl group-containing drug formulation, comprising:
- a quaternary ammonium preservative in an antimicrobially effective amount between 0.001% and 1.0% wt/vol of the formulation; and
- an ethoxylated alkyl phenol that conforms generally to the formula: $C_8H_{17}C_6H_4(OCH_2CH_2)_nOH$ where n has an average value of 40 in a stabilizing amount between 0.001% and 1.0% wt/vol of the formulation.

16. The preservative system of claim 15 wherein said preservative is benzalkonium chloride.

* * * * *

UNITED STATES PATENT AND TRADEMARK OFFICE
CERTIFICATE OF CORRECTION

PATENT NO. : 5,110,493
DATED : May 5, 1992
INVENTOR(S) : Cherng-Chyi Roger Fu and Deborah M. Lidgate It is certified that error appears in the above-indentified patent and that said Letters Patent is hereby corrected as shown below:

On the title page, under item [19], delete "Cherng-Chyi" and insert therefor --Fu --.

Item [75] Inventors: delete "Roger F. Cherng-Chyi", and insert therefor --Cherng-Chyi R. Fu --.

Signed and Sealed this

Twenty-fourth Day of August, 1993

Attest:

BRUCE LEHMAN

*Attesting Officer*   *Commissioner of Patents and Trademarks*